(12) United States Patent
Peters et al.

(10) Patent No.: US 7,765,003 B2
(45) Date of Patent: Jul. 27, 2010

(54) SYNCHRONIZATION CONTROL SYSTEM

(75) Inventors: William Suttle Peters, Auckland (NZ); Rodney Gordon Parkin, Crows Nest (AU)

(73) Assignee: Sunshine Heart Pty Ltd, St. Leonards, NSW (AU)

( * ) Notice: Subject to any disclaimer, the term of this patent is extended or adjusted under 35 U.S.C. 154(b) by 285 days.

(21) Appl. No.: 10/595,601

(22) PCT Filed: Oct. 28, 2004

(86) PCT No.: PCT/AU2004/001486

§ 371 (c)(1), (2), (4) Date: Apr. 28, 2006

(87) PCT Pub. No.: WO2005/042089

PCT Pub. Date: May 12, 2005

(65) Prior Publication Data
US 2007/0060787 A1 Mar. 15, 2007

(30) Foreign Application Priority Data
Oct. 31, 2003 (AU) .............................. 2003906070

(51) Int. Cl.
*A61M 1/10* (2006.01)
(52) U.S. Cl. .................. 607/18; 607/16; 607/17
(58) Field of Classification Search .................. 29/825; 381/67; 600/16, 17, 481, 513; 607/17, 57, 607/61
See application file for complete search history.

(56) References Cited

U.S. PATENT DOCUMENTS

| 3,552,383 | A | * | 1/1971 | Krueger et al. .............. 600/495 |
| 4,256,094 | A | * | 3/1981 | Kapp et al. .................. 601/152 |
| 4,459,977 | A | * | 7/1984 | Pizon et al. ................... 600/17 |
| 4,594,731 | A | * | 6/1986 | Lewkowicz .................. 381/67 |
| 4,763,646 | A |   | 8/1988 | Lekholm |
| 5,337,752 | A | * | 8/1994 | Reeves ....................... 600/513 |
| 5,447,523 | A |   | 9/1995 | Schaldach |
| 5,554,177 | A | * | 9/1996 | Kieval et al. ................. 607/17 |
| 5,722,930 | A | * | 3/1998 | Larson et al. ................. 600/16 |
| 5,792,195 | A |   | 8/1998 | Carlson et al. |
| 6,251,061 | B1 | * | 6/2001 | Hastings et al. ............... 600/16 |
| 6,553,263 | B1 | * | 4/2003 | Meadows et al. ............. 607/61 |
| 6,643,548 | B1 | * | 11/2003 | Mai et al. .................... 607/17 |

(Continued)

FOREIGN PATENT DOCUMENTS

EP 0080348 B2 9/1994

(Continued)

OTHER PUBLICATIONS

Luisada et al. On the Function of the Aortic Valve and the Mechanism of the First and Second Sounds. Japanese Heart Journal. vol. 18(1), Jan. 1977. pp. 81-91.*

(Continued)

*Primary Examiner*—Carl H Layno
*Assistant Examiner*—Luther G Behringer
(74) *Attorney, Agent, or Firm*—Faegre & Benson LLP

(57) ABSTRACT

A method of controlling the operation of a pulsatile heart assist device (14) in a patient (10). The method consisting of utilising sounds produced by the heart (12) to control the operation of the heart assist device (14).

10 Claims, 4 Drawing Sheets

U.S. PATENT DOCUMENTS

| | | |
|---|---|---|
| 7,169,109 B2 * | 1/2007 | Jansen et al. ................ 600/481 |
| 7,513,864 B2 * | 4/2009 | Kantrowitz et al. ........... 600/18 |
| 2003/1010549 | 6/2003 | Zhu et al. |

FOREIGN PATENT DOCUMENTS

| | | |
|---|---|---|
| EP | 1 129 736 A1 | 5/2001 |
| WO | WO 93/08874 | 5/1993 |
| WO | WO 98/14239 | 4/1998 |
| WO | WO 98/51367 | * 11/1998 |
| WO | WO 99/45981 | 9/1999 |

OTHER PUBLICATIONS

Anonymous. "Use of Heart Sounds as Input to Cardiac Assist Devices" Research Disclosures. Mar. 1995.*

* cited by examiner

SYNCHRONIZATION CONTROL SYSTEM

TECHNICAL FIELD

The present invention relates to methods and devices for controlling the operation of a pulsatile heart assist device or pacemaker.

The invention has been primarily developed for use in controlling the operation of extra-aortic counter-pulsation heart assist devices, for example as disclosed in the Applicant's International PCT Patent application no. PCT/AU00/00654 entitled "Heart assist devices, systems and methods". However, the invention is also suitable for use in controlling other heart assist devices, including but not limited to, intra-aortic balloons, aortomyoplasty, counter- and co-pulsation devices, or pacemakers or defibrillators or left ventricular assist devices or cardiac cycle monitoring.

BACKGROUND OF THE INVENTION

Counterpulsation heart assist devices must be controlled to operate in a predetermined time relationship with the pulsing of a patient's heart. For example, the counter-pulsation heart assist devices disclosed in the Applicant's above noted PCT patent application are configured to compress the aorta in synchrony with the diastolic period, the beginning of which is marked by closure of the aortic valve (which produces an audible sound known as second heart sound, or S2) to reduce the interior volume of the aorta during diastole. This compression increases systemic blood pressure, increases blood flow through the coronary arteries and increases diastolic output against the closed aortic valve. The compression of the aorta is alternated with periodic withdrawal of aortic compression following the R wave of the ECG (indicating ventricular depolarisation), around the time, known as presystole, of the closing of the mitral and tricuspid valves (audibly, the first heart sound, or S1) and opening of the aortic valve (marking the beginning of systole) to allow the aorta to return to its normal interior volume. This withdrawal of compression of the aorta at the time the heart is first ejecting blood from the left ventricle unloads the heart so that it can eject blood from the left ventricle more easily. Timing of deflation of the device in relation to the R wave or the detected first heart sound (S1), and inflation in relation to the second heart sound (S2) may be varied according to specific patients' physiology.

It will be apparent to those skilled in the art that the extent of heart assistance provided by counter-pulsation heart assist devices depends upon accurately timing the compression and decompression of the aorta relative to the timing of the native heart. In embodiments of the invention which relate to co-pulsation of the heart, the timing of compression of the heart must be also timed to its native rhythm.

Current devices rely on the ECG, particularly the R wave, to time deflation of the cuff, and inflation of the cuff may be timed to the dichrotic notch of the aortic pressure tracing, which indicates aortic valve closure. This methodology is severely limited in its application for control of heart assist devices and the like for a number of reasons:

1. The ECG is good for indicating the beginning of ventricular contraction, but does not indicate the end of systole. Further, whilst the T-wave indicates ventricular repolarisation, it is broad-based and not very accurate for timing purposes;
2. The systemic arterial blood pressure is very good at highlighting the time of aortic valve closure, but is only useful in a temporary manner, via a percutaneous arterial line, and is not suitable for long-term use;
3. The arterial pressure wave form is coupled to, but delayed, the more further peripherally the arterial pressure is measured from the aortic valve, and may not accurately describe the time of closure of the aortic valve; and
4. As the heart rate varies (particularly if the patient is suddenly exercising, or anxious, or the rhythm is in atrial fibrillation, or depending on the contractile state of the myocardium etc), time of opening and closure of the aortic valve after the R-wave of the ECG may vary significantly, thus whilst the beginning of systole can be relatively safely timed (and balloon deflation initiated), the timing of the beginning of diastole is not possible with ECG alone.

There is no reliable and accurate way to determine particularly the timing of aortic valve closure long-term in manner that allows patients to enjoy a good life-style whilst fitted with the device.

Methods are disclosed in U.S. Pat. Nos. 5,904,666 and 6,042,532, assigned to L. Vad Technology, Inc., to transduce the aortic pressure wave form every two to three minutes by taking a measurement of the dichrotic notch of the aortic blood pressure tracing. However, this requires the device functionality to be paused every 2-3 minutes to male measurements. This does not allow precise control of device function to specific heart beats, rather, timings are set for 2 minutes, until the measurement is re-done. Further, the dichrotic notch may not always be detected.

Another problem associated with components used to control partially implantable heart assist devices (i.e. having external drivers/controllers) is that the size, number, and rigidity of any percutaneous tubing or wires must be kept to a minimum to reduce the chance of infection and increase psychological acceptance of the devices. This can be achieved by the use of wireless transmission of cardiac cycle timing signals. However, the wireless telemetry associated with pacemakers is usually proprietary and unnecessarily complex, and is not suited for continuous discreet signal outputs.

It is an object of the present invention to provide methods and devices for determining and adjusting counterpulsation inflation timing by using detected heart sounds. In preferred embodiments, the heart sounds are monitored real-time to cause accurate beat-to-beat counterpulsation timing for each specific cardiac cycle, without interruption of heart assist functionality. Heart sounds may also be used intermittently to determine and reset the interval between R wave balloon deflation or inflation, either at fixed time intervals, or when there is a sustained change in the heart rate.

Another object is to provide, again at least in preferred embodiments, simple and economical wireless telemetry of the detected signals to an external device.

SUMMARY OF THE INVENTION

In a first aspect, the present invention provides a method of controlling the operation of a pulsatile heart assist device in a patient, consisting of utilising sounds produced by the heart to control the operation of the heart assist device.

Preferably, the method uses a combination of R-wave detection and heart sound detection to control the operation of the heart assist device. Alternatively, the heart assist device may be completely controlled by utilising both the S1 and S2 sounds of the heart to both stop and start the heart assist device.

In a second aspect, the present invention provides a method of controlling the operation of a pulsatile heart assist device in a patient, consisting of electrically detecting the R-wave of the patient's heart rhythm and producing a signal to initiate a change in the pulsatile status of the heart assist device, and detecting a sound or pressure wave created by the closure of the patient's aortic valve and producing a signal to return the heart assist device to the pulsatile status it had before the preceding R-wave.

In a third aspect, the present invention provides a method of controlling the operation of a pulsatile heart assist device with a multi-channel digital signal processor and transmitter (DSPT), the DSPT being of the type having an ECG channel and a phonocardiographic (PCG) channel, the DSPT being at least adapted to normally sense an electrical signal indicative of cardiac rhythm through the ECG channel, and to normally sense heart sounds through the PCG channel, and to transmit signals to an external receiver, the method comprising the steps of:

operatively connecting the DSPT bipolar ECG lead to a patient's heart; and operatively connecting the DSPT microphone to the patient's heart, whereby, after detecting an R-wave via the ECG channel, the DSPT issues a R-wave signal to the heart assist device controller to control the timing of the pulsation of the heart assist device, and whereby, after detecting a heart sound via the PCG channel, the DSPT issues a heart sound signal to the heart assist device controller to control the timing of the pulsation of the heart assist device.

The DSPT is preferably adapted to normally sense heart sounds through the PCG channel in the range of 20-500 Hz.

The DSPT is preferably able to receive as well as transmit, more preferably the DSPT has parameter settings adjusted within ranges, for detecting the R-wave and the heart sounds, and for the output signals.

The ECG lead connected to the patient's heart can be epicardial or endocardial or attached to an implanted heart assist device itself. In another embodiment sensors for the collection of an ECG signal may be embedded into the surface of a heart assist device applied to the heart or another part of the patient's body from which an ECG signal may be received.

The DSPT microphone may be internal to the patient's body. In this case connection to the patient's heart can be epicardial or endocardial, in the manner of a pacing lead, or attached to the implanted device itself, and, in this embodiment, is preferably located within 50 mm of the cardiac valves, and more preferably without the lung between the microphone and the patient's heart.

Alternatively the microphone may be positioned outside the body of the patient. The heart sounds and ECG to control an external gas-driven extra-aortic balloon pump may use an external microphone placed in the lumen of the extra aortic balloon or the gas line leading to it. The implanted gas line and balloon acts as a very efficient 'stethoscope', and heart sounds can be detected intermittently or continuously, and sent directly to a controller positioned outside the patient's body. Similarly, rather than requiring an implanted signal processor and transmitter, a percutaneous ECG lead may be used to directly transmit the ECG signal to the controller. The ECG lead may be combined with the percutaneous gas line or can be separate from the gas line. In either embodiment, it is preferable that there is a releasable and sealable connection for gas line and ECG lead under the skin, so that in the event of infection or non-use, the percutaneous lines can be removed, whilst leaving the gas line and ECG lead implanted for latter re-connection if required.

The DSPT is preferably also able to receive signals from an external device to adjust digital signal processing variables within the DSPT for detecting R-wave and heart sounds.

Preferably the DSPT has a battery of sufficient life that the DSPT can be removed and replaced, independent of the cardiac sensing leads, or that the DSPT has a rechargeable battery that can be recharged by induction, or Transcutaneous Energy Transfer (TET).

Further, the DSPT may communicate directly with an implanted controller, such as is contemplated with an implanted electrohydraulic Extra Aortic Balloon Pump (EABi) —the controller and the ECG and microphone may all be contained within the pump to limit the need for any leads, and the pump positioned, as intended, in the medial right chest, with one aspect of the pump (containing hermetically sealed microphone and ECG electrodes) against the right heart structures In a fourth aspect, the present invention provides a dual channel DSPT configured for use in controlling the operation of a pulsatile heart assist device, the DSPT being of the type having an ECG channel and a phonocardiographic (PCG) channel, the DSPT being at least adapted to normally sense an electrical signal indicative of cardiac rhythm through the ECG channel, and to normally sense heart sounds through the PCG channel, and to transmit signals to an external receiver to control the timing of the pulsation of the heart assist device. Signals may alternatively be directly sent to an implanted controller.

The DSPT is preferably adapted to normally sense heart sounds through the PCG channel in the range of 20-500 Hz.

The DSPT is preferably able to receive as well as transmit. More preferably, the DSPT has parameter settings adjustable within ranges, for detecting the R-wave and the Heart Sounds, and for the output signals.

The DSPT may have other channels for detecting aortic and left ventricular blood pressure and for movement of the aortic or ventricular walls, and signals from these channels may also be interpreted to control heart assist device functioning.

The heart assist device may be a co-pulsation device (such as an LVAD or a cardiac compression device) in which case the pulsations are in synchrony with the heart's native rhythm or it may be a counter-pulsation device in which the pulsations are out of phase with the heart's native rhythm. In the former configuration, the heart assist device may be of the type applying pulsatile compression of the heart itself. In the latter configuration, the heart assist device may be of the type adapted to apply pulsatile compression to a blood vessel either by compression of the outside of the vessels or by causing an intra-luminal device to expand and thereby cause blood volume displacement and pressure change in the systemic arterial system.

In a fifth aspect, the present invention provides means for controlling a co-pulsation or counter-pulsation heart assist device, the means including:

a co- or counter-pulsation heart assist device;

a controller for the heart assist device; and a DSPT of the type at least adapted to normally sense an electrical signal indicative of cardiac rhythm through an ECG channel and a sound signal indicative of heart sounds S1 and/or S2 through a PCG channel, and to issue identifiable signals to the controller, in which the DSPT is set to issue pacing signals from the ventricular circuit at a minimum rate which is below a physiologically sensible rate in the event that the atrial circuit is unable to sense a rhythm signal from the patient's ventricle, and the controller is set to turn off the heart assist device in the event that the pacing signals that the controller receives from the DSPT are at a rate below a predetermined rate which is above the minimum rate.

By adopting this approach if the controller is not sensing any signals at all it may mean that the controller has become disconnected from the DSPT or that the DSPT or the controller has run out of battery. As the latter condition can usually be detected readily, and in advance, the cause of the lack of signals can usually be rapidly identified. Alternatively if the signals fall to the minimum rate, at which time the device will have stopped, it can indicate there is a fault condition present in the pacing lead or the pacemaker or that the patient has died.

This rapid isolation of the cause of malfunction can assist in rapidly correcting the condition causing the malfunction. In the case of a patient dying it will prevent the heart assist device continuing to operate after death.

The DSPT is preferably adapted to normally sense heart sounds through the PCG channel in the range of 20-500 Hz.

The DSPT is preferably able to receive as well as transmit, more preferably the DSPT has parameter settings adjustable within ranges, for detecting the R-wave and the Heart Sounds, and for the output signals.

The method preferably includes implanting the DSPT under the skin in front of the shoulder in the delto-pectoral region or over the abdomen

BRIEF DESCRIPTION OF THE DRAWINGS

Preferred forms of the present invention will now be described, by way of examples only, with reference to the accompanying drawings, wherein.

DETAILED DESCRIPTION OF THE PREFERRED EMBODIMENTS

By way of further background, the DSPT has the basic modalities of sensing, transmitting, and programmability.

Sensing is the capability to detect and interpret a patient's native heart electro- and phonocardiograms (ECG's and PCG's respectively). An implanted sensing lead detects the patient's native heart electrical activity and transmits it to the DSPT circuitry. The firmware and/or software within the DSPT unit interprets the patient's R-wave and transmits a signal indicating R-wave detection. An implanted microphone lead detects the patient's native heart sounds and transmits it to the DSPT circuitry. The firmware and/or software within the DSPT unit interprets the patient's heart sounds and transmits a signal indicating S1 and S2 detection.

Programmability is the capability to allow a physician to adjust the DSPT's sensing and transmitting functions to the patient's individual needs. This is achieved by using a laptop-like device, typically called a programmer, that has an input device that is placed over the patient's skin in the vicinity of an implanted DSPT. The programmer transdermally communicates with the patient's DSPT, using either auditory (tonal) or electromagnetic pulses, and allows the physician to manipulate the DSPTs settings as needed.

The ECG sensing system is expected to be able to work in the presence of a dual-chambered pacemaker providing pacing control over the patient's rhythm because their native rhythm would be deficient or absent.

Combination pacemakers and internal cardioverter/defibrillators (ICDs) can, when ventricular tachycardia or VF is sensed, either attempt to "overdrive" pace a patient out of the rhythm (i.e. pace with a strong impulse that will override the patient's native rhythm and slowly decrease rate to control the patient's rhythm) or shock the heart out of the rhythm and then pace it.

Figure 1:
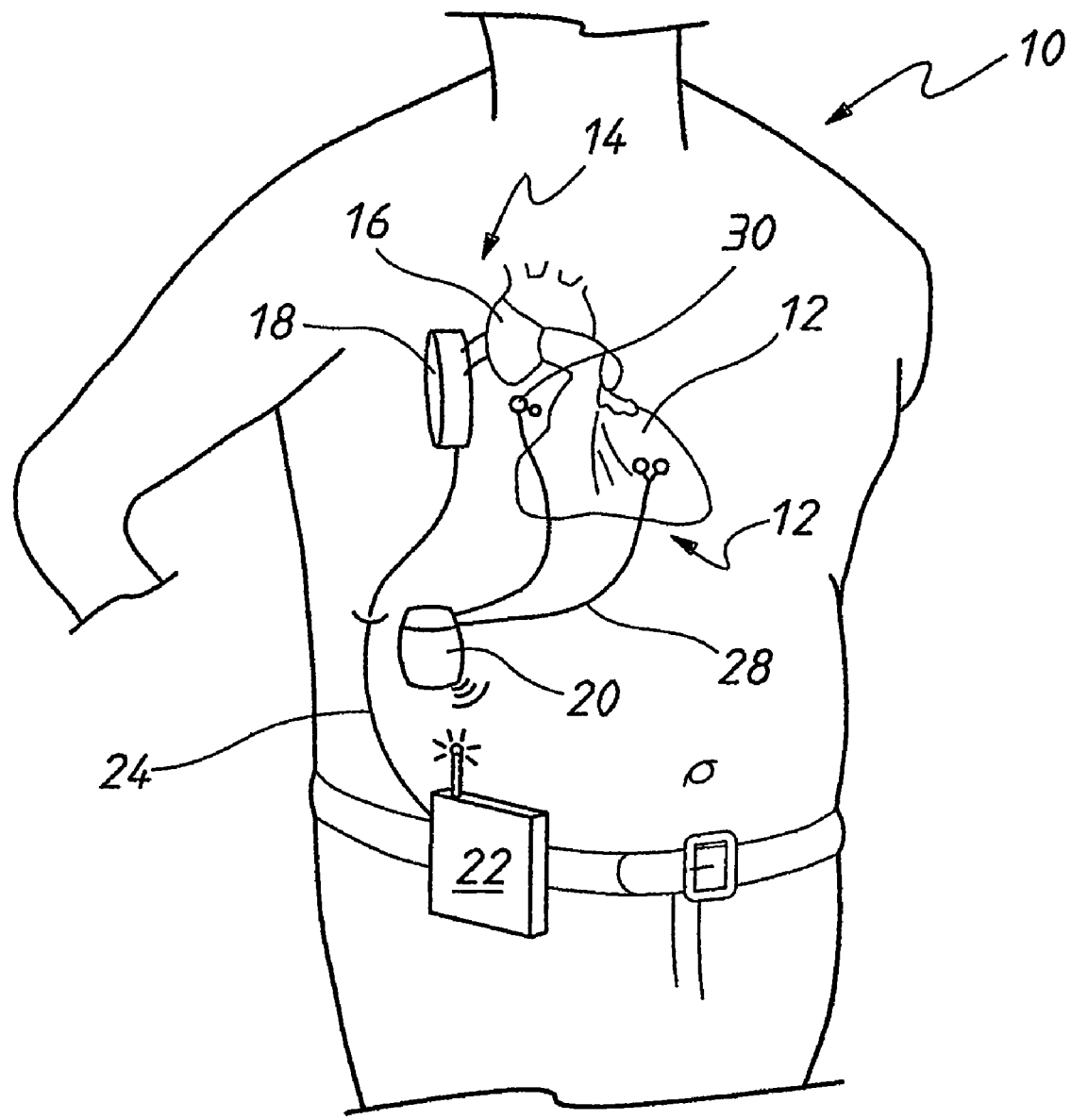
FIG. 1 is a cut away view of a patient with a heart assist device controlled in accordance with a first embodiment of the invention.

A first embodiment of the invention will now be described with reference to FIG. 1, which shows a patient 10 with a heart 12. The output of the heart 12 is assisted by a pulsatile, fully implantable, heart assist device, indicated generally by the reference numeral 14. The heart assist device 14 has an aortic cuff 16 around the patient's ascending aorta. The cuff 16 is essentially the same as those disclosed in the Applicant's previously referred to International PCT Patent application no. PCT/AU00/00654. The cuff 16 is driven by a pump 18, which essentially the same as those disclosed in the Applicant's International PCT Patent application no. PCT/AU02/00974 entitled "A fluid pressure generating means". Also shown is an implanted DSPT 20. The pump 18 is powered/controlled by an external battery/controller 22 via a percutaneous electrical cable 24. The DSPT 20 transmits RF signals to the controller 22 of the heart assist device 14.

The DSPT 20 has an ECG channel connected to sensing lead 26 and an PCG channel connected to the microphone lead 28.

The DSPT ECG channel is connected, via the sensing lead 26, to the epicardial surface of the ventricle of the patient's heart 12 and the DSPT PCG channel is connected, via the microphone lead 28, to a microphone 30 implanted in close proximity to the aortic valve, exterior to the aortic root.

In operation, the DPST 20 detects an R-wave (i.e. the R wave of the ventricle) through the ECG channel, then waits for a predetermined time (for example from 0-30 msec) before transmitting a signal to the controller 22 which in turn controls the pulsation of the heart assist device 14. It will be understood that, in the above configuration, the DSPT 20 will always issue the signal to the controller 22 and the controller may be programmable as to what action is taken when this signal is received. If desired, the DSPT 20 may issue the signal from the ECG channel immediately upon receiving the sensed signal in the ECG channel. In this case there would be a variable delay programmable into the controller 22 to ensure that the time at which the heart assist device 14 is actuated is correctly timed for that individual patient.

Further, the DSPT 20 is designed to allow correct sensing of cardiac activity even in the presence of electrical or pressure or other noise interference. It is also designed to withstand defibrillation pulses without damage.

In the preferred form shown, the heart assist device 14 is a counter pulsation device in which the pulsations are out of phase with the heart's native rhythm.

The controller 22 is configured to turn the heart assist device off in the event that the pacing signal received from the ventricular circuit falls below a rate below the minimum rate, say 40 beats per minute. If the controller 22 indicates that it is not receiving any pacing signal this will be typically indicative of the DSPT 20 not transmitting to the controller 22 or a gross malfunction of the DSPT 20 or its leads 26 or 28.

Figure 2:
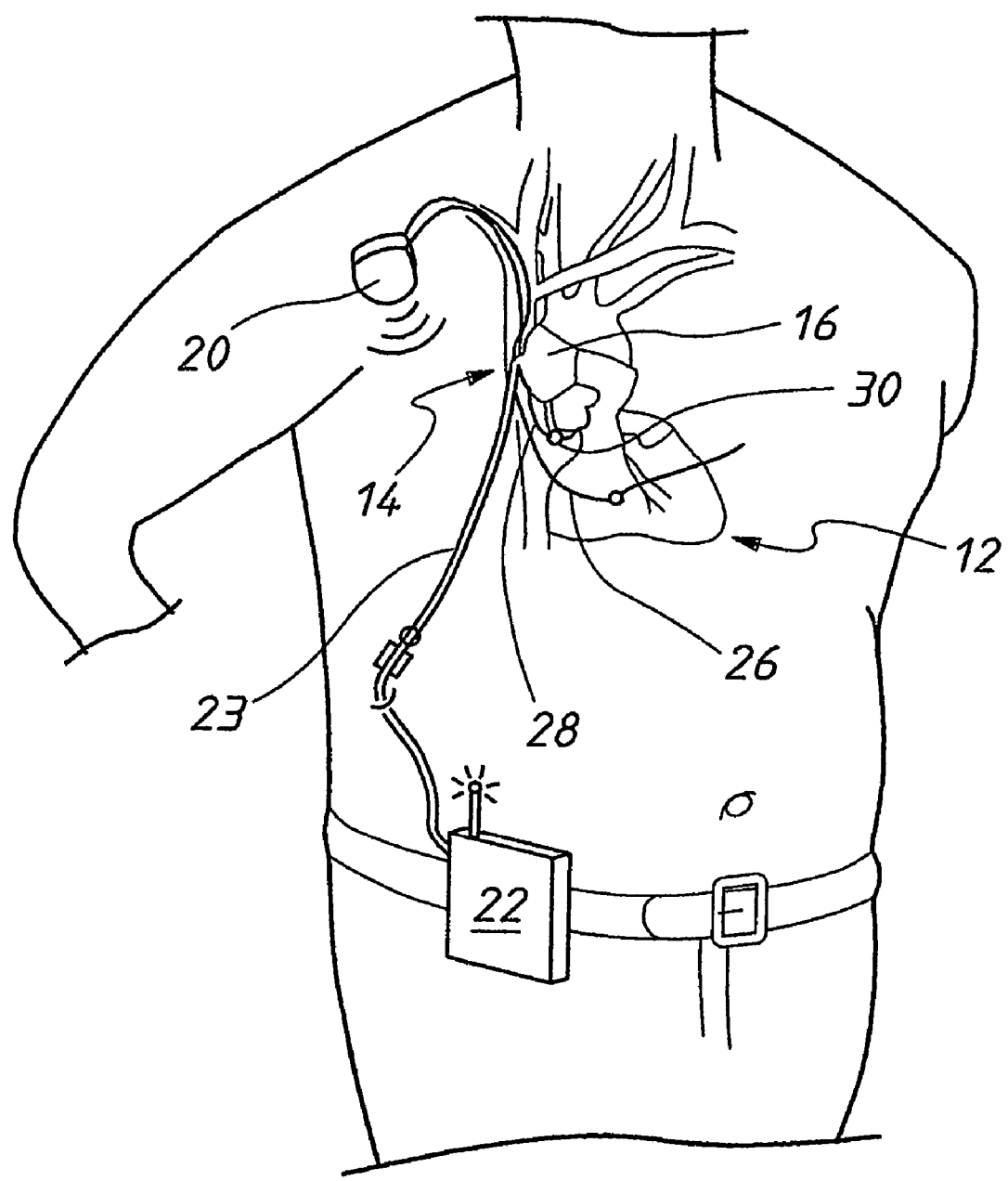
FIG. 2 is a cut away view of a patient with a heart assist device controlled in accordance with a second embodiment of the invention.

A second embodiment of the invention will now be described with reference to FIG. 2, in which like features to the first embodiment will be indicated with like reference numerals. FIG. 2 shows a patient 10 with a heart 12. The output of the heart 12 is assisted by a pulsatile, partially implantable, heart assist device, indicated generally by the reference numeral 14. The heart assist device 14 has an aortic cuff 16 around the patient's ascending aorta. The cuff 16 is essentially the same as those disclosed in the Applicant's previously mentioned PCT Patent application. The cuff 16 is driven by an external pump and controller 22 via a percutaneous gas line 23. These types of pumps and controllers are well known to persons skilled in the art and will not be described in further detail herein. A battery (not shown) is also mounted within the casing of the pump and controller 22.

Also shown is the DSPT 20, which has an ECG channel connected to the sensing lead 26 and a PCG channel connected to the microphone lead 28. The DSPT transmits signals to the controller 22 of the heart assist device 14.

The DSPT ECG channel is connected, via the sensing lead 26, to the endocardial surface of the ventricle of the patient's heart 12 and the DSPT PCG channel is connected, via the microphone lead 28, to a microphone 30 implanted in close proximity to the aortic valve, also via the endocardium. These leads may be placed via the subclavian or jugular vein, and positioned in the right heart chamber, either the right atrium, right ventricle, or in the coronary sinus.

In operation, the DSPT 20 detects an R-wave (i.e. the R wave of the ventricle) through the ECG channel, then waits for a predetermined time (for example from 0-30 msec) before transmitting a signal to the controller 22 which in turn controls the pulsation of the heart assist device 14. It will be understood that, in the above configuration, the DSPT 20 will always issue the signal to the controller 22 and the controller may be programmable as to what action is taken when this signal is received. If desired, the DSPT 20 may issue the signal from the ECG channel immediately upon receiving the sensed signal in the ECG channel. In this case there would be a variable delay programmable into the controller 22 to ensure that the time at which the heart assist device 14 is actuated is correctly timed for that individual patient.

The DSPT 20 is implanted under the skin, preferably in the front of the shoulder, over the delto-pectoral region, or under the skin over the abdomen. This location makes it easy to locate a battery recharging coil or a programmer 'wand' (not shown).

Figure 3:
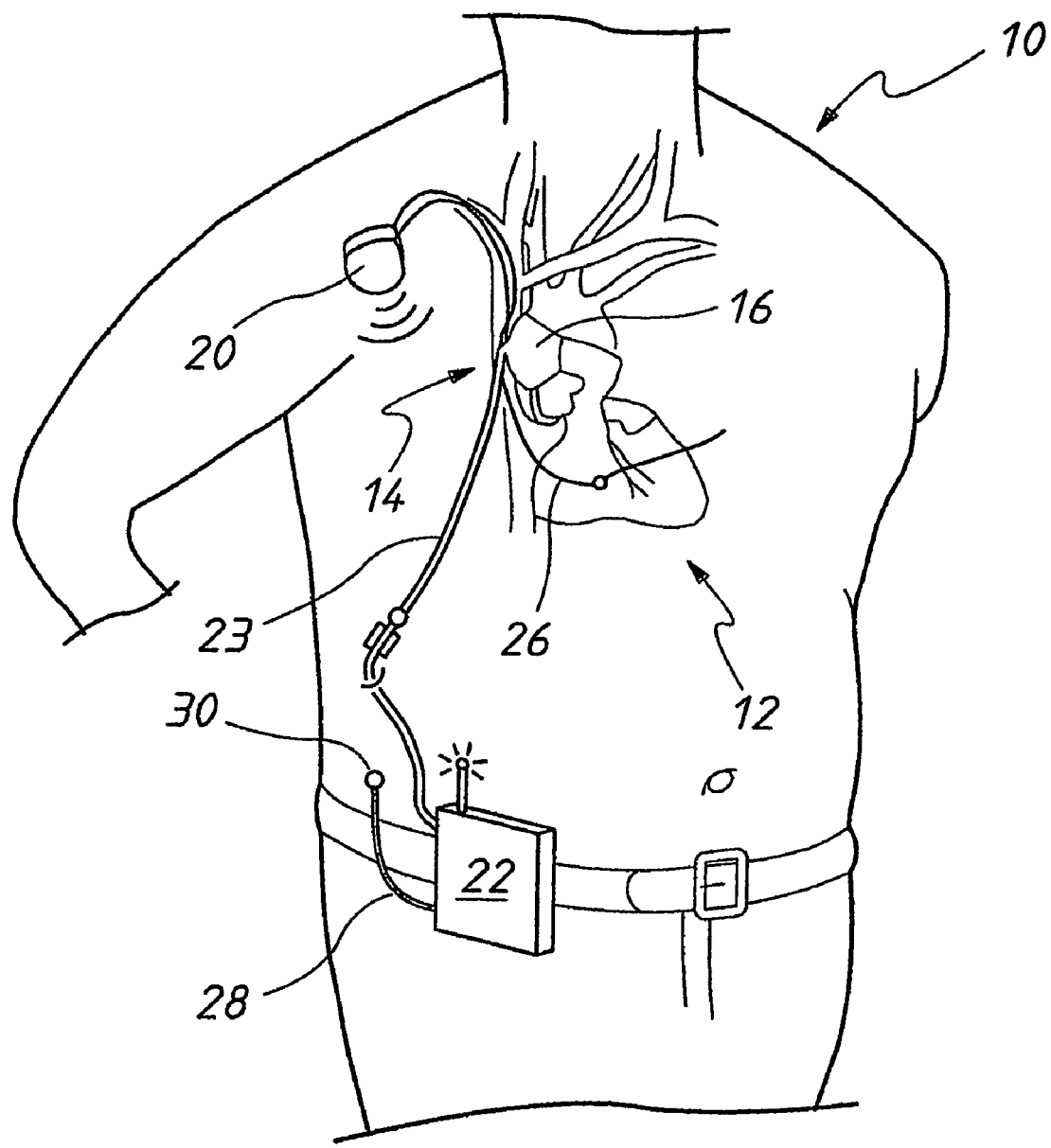
FIG. 3 is a cut away view of a patient with a heart assist device controlled in accordance with a third embodiment of the invention.

A third embodiment of the invention will now be described with reference to FIG. 3, in which like features to the second embodiment will be indicated with like reference numerals. The third embodiment is, and operates, very similar to the second embodiment except the microphone 30 detects heart sounds in the gas line 23 and the external controller 22 transmits corresponding signals to the PCG channel of the implanted DSPT 20.

A fourth embodiment of the invention will now be described with reference to FIG. 4, in which like features to the third embodiment will be indicated with like reference numerals. The fourth embodiment is very similar to the third embodiment except the heart assist device 14 is controlled using only heart sounds in the gas line 23 detected by the microphone 30. (i.e. no ECG signals are monitored). In this embodiment, the microphone 30 is positioned within an externally positioned housing 32 which also contains the pump and controller 22 and the DSPT 20. The microphone 30 is in direct communication with the gas line 23 which acts as a "stethoscope" transmitting sound from the heart 12 to the externally mounted microphone 30. In operation, the microphone 30 receives the S1 sound as the aortic valve opens and the DSPT transmits a signal indicative of that reception to the controller and pump 22. The heart assist device 14 is deflated on receipt of the DSPT signal. When the microphone 30 receives the S2 sound indicative of the aortic valve closing the DSPT signals the controller and pump 22 to reinflate the heart assist device 14. In this embodiment of the invention the DSPT may contain software to filter out sounds other than the S1 and S2 sounds or the system may be such that the pump is periodically stopped for a single heart beat to allow detection of the S1 and S2 sounds and the controller and pump 22 then operates for a predetermined time on the basis of the timing detected during the period that the pump was inoperative.

Figure 4:
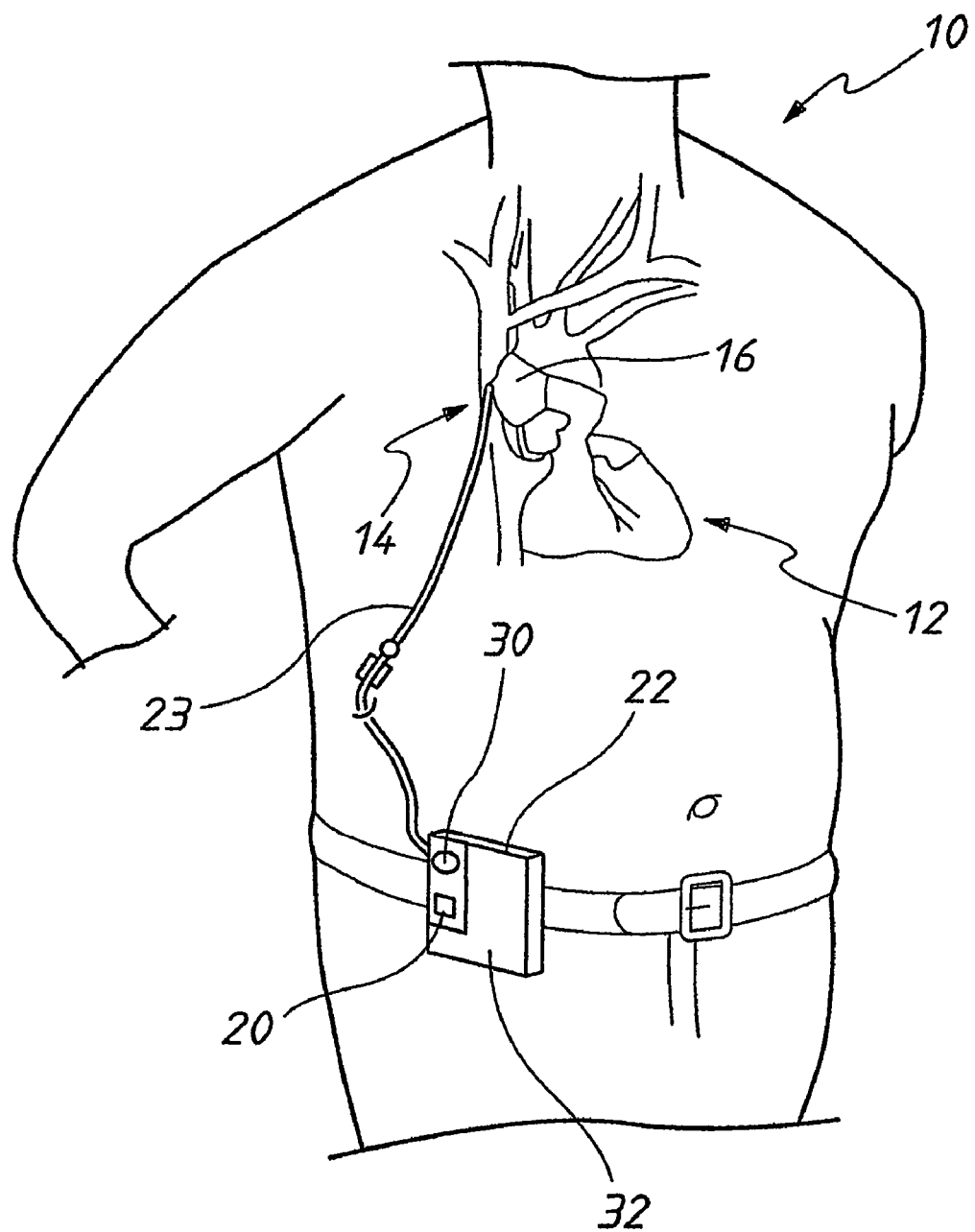
FIG. 4 is a cut away view of a patient with a heart assist device controlled in accordance with a fourth embodiment of the invention, in which an externally mounted housing containing the DSPT and the pump and controller is shown partially cut-away.

The arrangement shown in FIG. 4 may be altered by providing an ECG lead which extends from the heart 12 to the housing 32. In this case the DSPT will operate on the basis of the ECG detection of the R wave and on reception of the S2 sound. The ECG lead will preferably be disposed within the lumen of the gas line at the point of exit from the patient's body or be attached to the gas line. This means that there is only one point of percutaneous access into the patient. The ECG lead may also be brought out adjacent the gas line.

The detection of both R-wave and heart sounds dramatically improves the accuracy of timing the heart assist device accurately, from beat-to-beat, to events in the cardiac cycle such as the beginning of systole and diastole. Further, the signal transmission arrangement provides a cost effective and robust wireless telemetry system with minimal patient discomfort. Also, as the percutaneous gas line does not have to carry any internal leads, it can be made relatively smaller and more flexible to improve patient comfort.

It will be appreciated by the person skilled in the art that numerous variations and/or modifications may be made to the invention as shown in the specific embodiment without departing from the spirit or scope of the invention as broadly described. The present embodiment is therefore to be considered in all respects as illustrative and not restrictive.

For example, although epicardial leads are shown in FIG. 2, one lead could be endocardial and the other epicardial or visa versa.

The invention claimed is:

1. In an apparatus for controlling the pulsations of a heart assist device to alternate between compression of a blood vessel and withdrawal of compression of the blood vessel in a timed relationship with the pulsing of a patient's heart, wherein said heart assist device comprising: a pump for generating fluid pressure; an inflatable cuff for applying said pressure to blood in a blood vessel; a fluid for transmitting said pressure between said pump for generating fluid pressure and said inflatable cuff for applying said pressure, the improvement comprising a microphone positioned within said fluid, the microphone being adapted to detect heart sounds in said blood vessel conveyed to said microphone through said fluid.

2. The apparatus as claimed in claim 1, wherein said heart sounds detected by the microphone are utilized in controlling the operation of said heart assist device.

3. The apparatus as claimed in claim 2, wherein said fluid is a gas.

4. The apparatus as claimed in claim 1, wherein the microphone is positioned within said fluid within, or proximal to, the pump.

5. The apparatus as claimed in claim 4, wherein said pressure is applied to said inflatable cuff and said inflatable cuff in turn applies said pressure to the exterior of said blood vessel.

6. The apparatus as claimed in claim 1, wherein said pressure is directly applied to the exterior of said blood vessel.

7. The apparatus as claimed in claim 6, wherein said pressure is applied to the exterior of an aorta.

8. The apparatus as claimed in claim 1, wherein said heart assist device initiates a change in its pulsatile state in response to electrical detection of an R-wave in a patient's heart rhythm and returns to the pulsatile state it had before the preceding R-wave in response to said microphone detecting said heart sound created by closure of the patient's aortic valve.

9. The apparatus as claimed in claim 1, wherein said inflatable cuff includes a flexible membrane and said flexible membrane applies said pressure to the blood in the blood vessel.

10. The apparatus as claimed in claim 1, wherein said fluid is a liquid.

\* \* \* \* \*